(12) United States Patent
Yang et al.

(10) Patent No.: US 10,745,720 B2
(45) Date of Patent: *Aug. 18, 2020

(54) PRODUCTION METHOD FOR TAGATOSE

(71) Applicant: CJ CHEILJEDANG CORPORATION, Seoul (KR)

(72) Inventors: Sung Jae Yang, Gwangmyeong-si (KR); Yang Hee Kim, Bucheon-si (KR); Seong Bo Kim, Seoul (KR); Seung Won Park, Yongin-si (KR); Il Hyang Park, Seoul (KR); Min Hae Kim, Incheon (KR); Young Mi Lee, Bucheon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 159 days.

This patent is subject to a terminal disclaimer.

(21) Appl. No.: 14/892,710

(22) PCT Filed: Jun. 3, 2014

(86) PCT No.: PCT/KR2014/004970
§ 371 (c)(1),
(2) Date: Nov. 20, 2015

(87) PCT Pub. No.: WO2014/196811
PCT Pub. Date: Dec. 11, 2014

(65) Prior Publication Data
US 2016/0138053 A1 May 19, 2016

(30) Foreign Application Priority Data

Jun. 5, 2013 (KR) .................. 10-2013-0065002
Jun. 3, 2014 (KR) .................. 10-2014-0067867

(51) Int. Cl.
*C12P 7/26* (2006.01)
*C12P 19/24* (2006.01)
*C12P 19/02* (2006.01)
*C07C 45/81* (2006.01)
*C12N 9/90* (2006.01)

(52) U.S. Cl.
CPC .............. *C12P 7/26* (2013.01); *C07C 45/81* (2013.01); *C12N 9/90* (2013.01); *C12P 19/02* (2013.01); *C12P 19/24* (2013.01); *C12Y 501/03* (2013.01); *Y02P 20/582* (2015.11)

(58) Field of Classification Search
None
See application file for complete search history.

(56) References Cited

U.S. PATENT DOCUMENTS 10,196,626 B2 * 2/2019 Yang ................. C12P 19/02
2010/0285539 A1 * 11/2010 Kim .................. C07H 1/08
435/94

2013/0081613 A1 4/2013 Xu
2016/0138053 A1 * 5/2016 Yang ................. C12P 7/26
435/148
2019/0136223 A1 * 5/2019 Yang ................ C12P 19/02

FOREIGN PATENT DOCUMENTS

| JP | 2004-82 A | 1/2004 |
| JP | 2004-535205 A | 11/2004 |
| JP | 2010-511699 A | 4/2010 |
| KR | 10-2006-0125971 A | 12/2006 |
| KR | 10-2008-0053708 A | 6/2008 |
| KR | 10-2009-0125004 A | 12/2009 |

OTHER PUBLICATIONS

Kim et al. Appl Biochem Biotechnol. 2011, 163:444-451.*
Rodionova et al. Environmental Microbiology, 2012, 14(11), 2920-2934.*
Kim et al., "Novel Activity of UDP-Galactose-4-Epimerase for Free Monosaccharide and Activity Improvement by Active Site-Saturation Mutagenesis", Appl Biochem Biotechnol, Aug. 19, 2011, vol. 163, pp. 444-451.
Office Action dated Nov. 22, 2016 of corresponding Japanese Patent Application No. 2016-518272—6 pages.
Extended European Search Report dated Jan. 27, 2017 of European Patent Application No. 14807891.8—6 pages.
NCBI, Reference Sequence: WP_015918744.1, May 21, 2013.
Kim et al., "Novel Activity of UDP-Galactose-4-Epimerase for Free Monosaccharide and Activity Improvement by Active Site-Saturation Mutagenesis", Applied Biochemistry and Biotechnology, 2011, vol. 163, No. 3, pp. 444-451.
Beerens, "Characterization and engineering of epimerases for the production of rare sugars", Ghent University, Faculty of Bioscience Engineering, Dissertation, Feb. 8, 2013.
Rodionova et al., "Tagaturonate—fructuronate epimerase UxaE, a novel enzyme in the hexuronate catabolic network in Thermotoga maritima", Environmental Microbiology, 2012, vol. 14, No. 11, pp. 2920-2934.
Wanarska et al., "A method for the production of D-tagatose using a recombinant Pichia pastoris strain secreting β-galactosidase from Arthrobacter chlorophenolicus and a recombinant L-arabinose isomerase from *Arthrobacter* sp. 22c", Microbial Cell Factories, 2012, vol. 11, No. 113, pp. 1-15.
International Search Report dated Sep. 1, 2014 of PCT/KR2014/004970 which is the parent application and its English translation—6 pages.
Yamanaka, "Sugar Isomerases: Part II Purification and Properties of D-Glucose Isomerase from Laciobacillus brevis", Agr. Biol. Chem., vol. 27, No. 4, p. 271-278, 1963.

* cited by examiner

*Primary Examiner* — Vera Afremova
(74) *Attorney, Agent, or Firm* — Knobbe Martens Olson & Bear LLP

(57) ABSTRACT

A method for producing tagatose comprises: a) performing epimerization of fructose using hexuronate C4-epimerase to obtain an epimerized product comprising tagatose; b) purifying the epimerized product; and c) crystallizing the purified epimerized product. The hexuronate C4-epimerase is an enzyme derived from Thermotoga maritima, Thermotoga neapolitana, Thermotoga thermarum or mutants thereof. The hexuronate C4-epimerase is produced from strains *Escherichia coli, Corynebacterum glutamicum, Aspergillus oryzae*, or *Bacillus subtilis*.

14 Claims, 11 Drawing Sheets

Specification includes a Sequence Listing.

PRODUCTION METHOD FOR TAGATOSE

TECHNICAL FIELD

The present invention relates to a method for producing tagatose from fructose, more particularly, to a method for producing tagatose by epimerization of fructose at the C4-position.

BACKGROUND ART

Tagatose has a natural sweet taste which is hardly distinguishable from sucrose and has physical properties similar to sucrose. However, ingested tagatose is not well absorbed in the small intestine and thus has a minimal impact on blood glucose level. Further, tagatose is a low calorie sweetener having about 30% the calories of sucrose. In addition, tagatose has a prebiotic effect that promotes growth of beneficial lactic acid bacteria through fermentation by intestinal microflora.

Only about 20% of ingested tagatose is absorbed in the small intestine and the remaining 80% fraction of tagatose reaches the large intestine where the intestinal microflora lives, and selectively promotes the production of lactic acid bacteria, thereby producing short chain fatty acids. Particularly, tagatose has a prebiotic property capable of producing large amounts of butyrate (up to 50% of the total short chain fatty acids) which can prevent colon cancer. Furthermore, tagatose is a natural sugar having a low-calorie value of 1.5 kcal/g and has attained GRAS (Generally Recognized As Safe) status under the U.S. Food and Drug Administration, thereby permitting use as a functional sweetener in foods, beverages, health foods, diet additives, and the like.

However, tagatose is not often found in nature and is a rare sugar present only in small amounts in dairy products and some plants. In order to use tagatose as a low-calorie and functional sweetener, it is essential to develop a method for mass production of tagatose from inexpensive raw materials.

Tagatose has conventionally been produced by isomerization of galactose. In order to economically afford galactose, studies have been carried out to develop various raw materials containing galactose, methods for attaining galactose and methods for producing tagatose using the raw materials. Lactose has been used as the most representative raw material for tagatose. However, the prices of lactose or lactose-containing products show a unique price pattern of repeating fall and rise due to various factors such as amounts of raw milk produced according to weather, demand for powdered milk, changes in lactose amount consumed in developing nations, and the like. Such price fluctuations in the raw milk market make the stable supply of raw materials for producing tagatose difficult. Accordingly, there is a need for a new method for producing tagatose using common raw materials (glucose, sucrose, fructose, and the like).

Korean Unexamined Patent Publication No. 10-2009-0125004 discloses a method for producing galactose by epimerization of glucose. Korean Unexamined Patent Publication No. 10-2006-0125971 discloses C3-epimerization of ketohexose. However, both documents fail to disclose a method for producing tagatose through C4-epimerization of fructose.

DISCLOSURE

Technical Problem

In the past, tagatose was produced from galactose decomposed from lactose or lactose-containing products and various other biological resources containing galactose. However, up to now, raw materials evaluated capable of being commercially produced or approaching commercialization in terms of stable supply of raw materials and investment efficiency are lactose or lactose-containing products (whey etc.). However, lactose or lactose-containing products undergo extreme price changes and have a problem in that stable supply of tagatose is not ensured due to recent rise in lactose consumption and price rise.

Further, a conventional chemical method for converting lactose into galactose has a limit in epimerization and a conventional enzymatic method also has a limit due to use of galactose.

Accordingly, it is an aspect of the present invention to provide a method for producing tagatose, which is more stable and economical while securing higher production efficiency than a typical method for producing tagatose.

Technical Solution

Embodiments of the present invention provide a method for producing tagatose, including: performing epimerization of fructose using hexuronate C4-epimerase to obtain an epimerized product including tagatose; purifying the epimerized product; and crystallizing the purified epimerized product.

Advantageous Effects

The present invention can provide a method for producing tagatose which is economical and has high yield using a common raw material, fructose, instead of lactose with violent price fluctuations, thereby reducing production costs.

In general, since it is well known in the art that fructose can be industrially produced from glucose or sucrose, raw materials suggested in the present invention encompass not only fructose but also raw materials entirely or partially containing fructose such that more economical production can be ensured. Namely, the present invention encompasses production of tagatose through enzymatic conversion of starch, crude sugar or sucrose.

Further, the present invention can produce tagatose from fructose, which ensures efficient mass production of tagatose attracting attention as important food materials.

EMBODIMENTS

Figure 1:
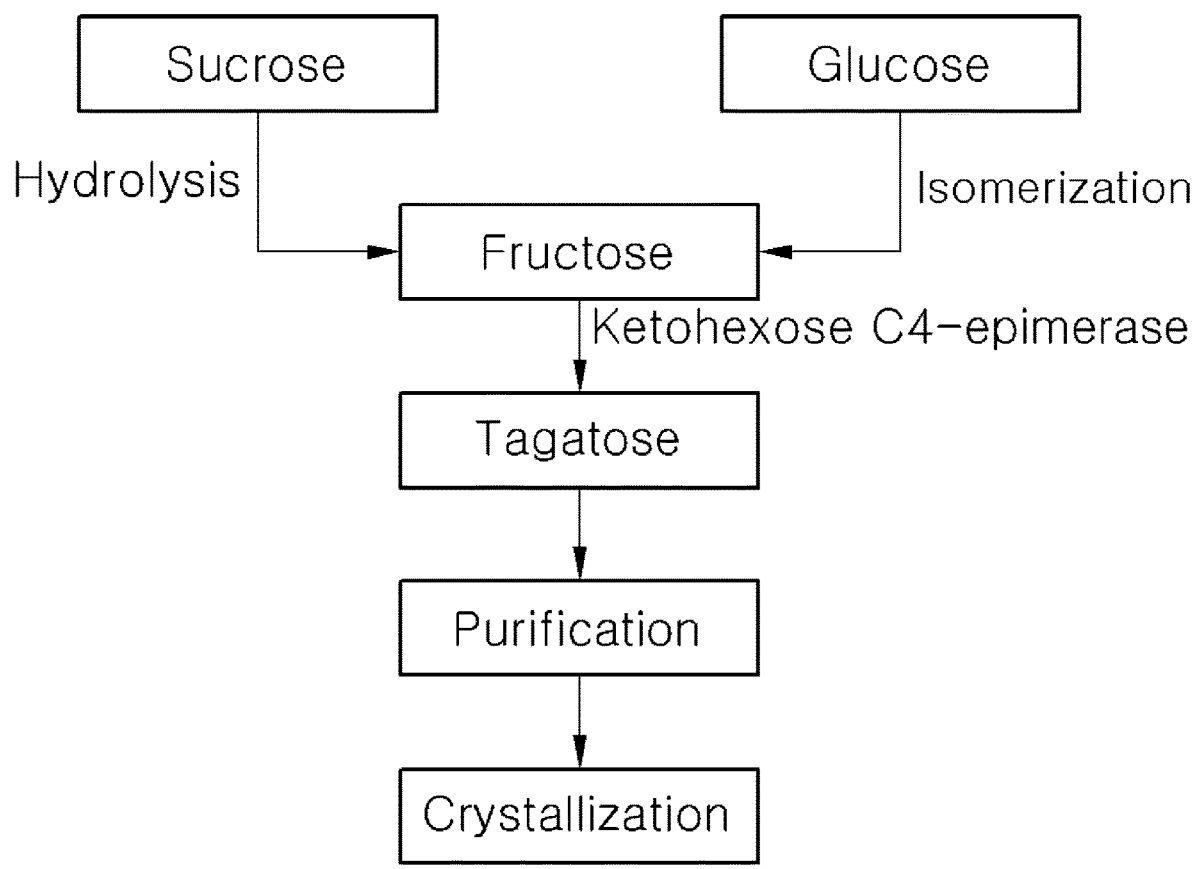
FIG. 1 is a flowchart of a process of producing tagatose in accordance with one embodiment of the present invention.

Hereinafter, the present invention will be described in more detail. Descriptions of details apparent to those skilled in the art having ordinary knowledge in this technical field or relevant field will be omitted herein.

As used herein, the term "$C_n$—" refers to a carbon position determined in accordance with carbon numbering prescribed by IPUAC nomenclature wherein n is an integer of 1 or more. For instance, "epimerization at carbon 4 position" is represented by "C4-epimerization".

In accordance with one embodiment of the present invention, a method for producing tagatose includes: a) performing epimerization of fructose using hexuronate C4-epimerase to obtain an epimerized product including tagatose; b) purifying the epimerized product; and c) crystallizing the purified epimerized product.

In general, monosaccharides may be classified as aldohexoses and ketohexoses. Aldohexose refers to an aldose that has six carbon atoms and an aldehyde group at one end thereof. Examples of aldohexose include glucose, galactose, allose, gulose, altrose, mannose, talose, and idose, without being limited thereto. Further, a ketohexose as used herein refers to a monosaccharide having six carbon atoms and a ketone group. Examples of ketohexose include fructose, tagatose, psicose, and sorbose, without being limited thereto. Preferably, fructose is used as a ketohexose. As used herein, both fructose and tagatose refer to D-fructose and D-tagatose, unless otherwise specified.

According to another embodiment of the present invention, fructose is obtained from sucrose or glucose. Accordingly, the present invention provides a method for producing tagatose with high yield using common and inexpensive raw materials such as glucose, fructose, sucrose, or the like, thereby enabling mass production of tagatose.

Accordingly, the method may further include, before step a), performing hydrolysis of sucrose to obtain fructose. Enzymes used in hydrolysis may include at least one selected from the group consisting of β-D-fructosidases, such as β-fructofuranosidase, invertase, and saccharase; sucrase, α-glucosidase, and α-D-glucohydrolase, without being limited thereto.

Further, the method may further include, before step a), performing isomerization of glucose to obtain fructose. The enzymes used in isomerization (isomerases) may include glucose isomerase or phosphoglucoisomerase, without being limited thereto.

The hexuronate C4-epimerase according to the present invention may include *Thermotoga* sp. derived enzymes or variants thereof. Specifically, the hexuronate C4-epimerase may include *Thermotoga maritima, Thermotoga neapolitana,* or *Thermotoga thermarum* derived enzymes or variants thereof.

Further, the hexuronate C4-epimerase may be obtained, for example, by transforming a strain (microorganism) such as *Escherichia coli* (*E. coli*) and the like with genomic DNA represented by SEQ ID NOs: 1 to 3, culturing the transformed strain to obtain a cultivated cell, disrupting the cultivated cell and purifying the cell extract through a column and the like. The strains for transformation may include *Escherichia coli, Corynebacterum glutamicum, Aspergillus oryzae,* or *Bacillus subtilis,* and the like. Examples of the *E. coli* transformed strains include *E. coli* BL21(DE3)pET21a-TM (accession number: KCCM11542P), *E. coli* BL21(DE3) pET21a-TN (accession number: KCCM11543P), or *E. coli* BL21(DE3) pET28a-TN(m) strain (accession number: KCCM11544P), and the like. The strains *E. coli* BL21(DE3)pET21a-TM, *E. coli* BL21(DE3) pET21a-TN and *E. coli* BL21(DE3) pET28a-TN(m) were deposited at Korean Culture Center of Microorganisms (KCCM) (361-221 Hongje 1-dong, Seodaemun-gu, Seoul, Korea), which is an international depository, on May 23, 2014 as accession numbers KCCM11542P, KCCM11543P, and KCCM11544P, respectively.

Thus, a further embodiment of the present invention relates to each deposited strain of *E. coli* BL21(DE3) pET21a-TM (accession number: KCCM11542P), *E. coli* BL21(DE3) pET21a-TN (accession number: KCCM11543P), or *E. coli* BL21(DE3) pET28a-TN(m) (accession number: KCCM11544P).

Epimerization of fructose using hexuronate C4-epimerase may be performed at 60° C. to 90° C. and pH 5 to 8, preferably at pH 6 to 8 and high temperature such as 70° C. to 90° C. or 75° C. to 90° C. Within this range, enzymatic reaction can be performed at a relatively high temperature, thereby minimizing microorganism contamination in the process, thereby providing effects of enhancing solubility of ketohexoses used as substrates while maximizing a reaction rate and a conversion rate of enzymes. The effect of reaction temperature on enzyme activity is described with reference to FIG. 7. As temperature increases, C4-epimerase activity also increases. However, at about 90° C., enzyme activity may be rapidly declined.

Figure 8:
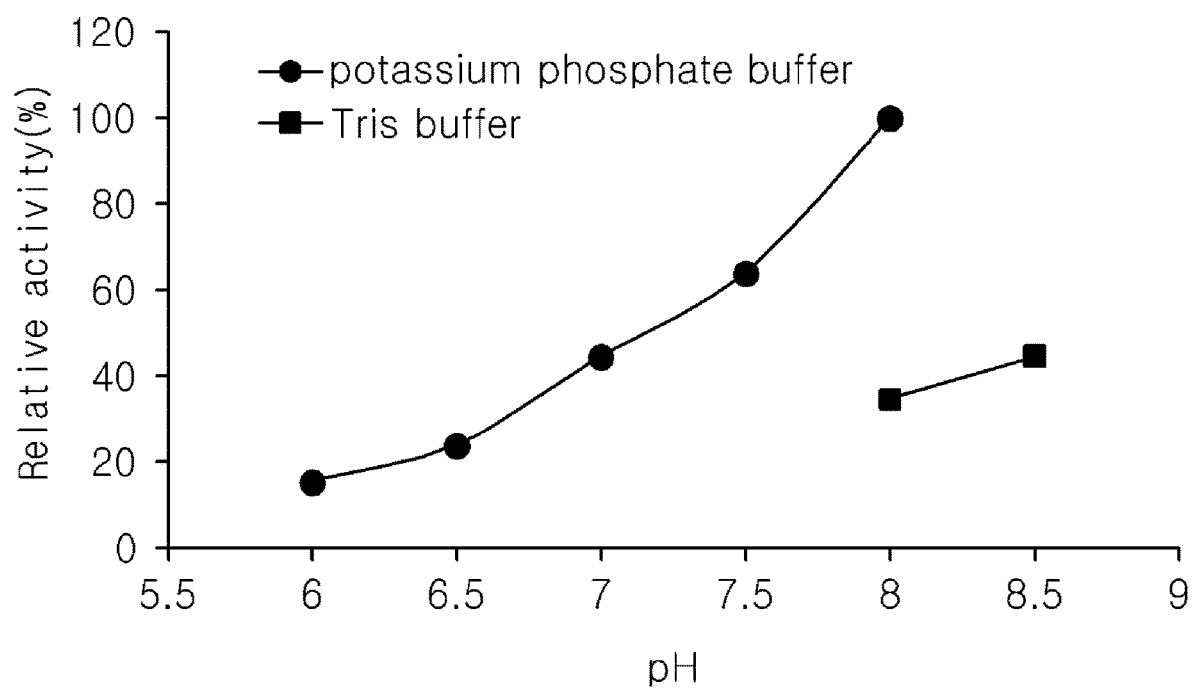
FIG. 8 is a graph depicting C4-epimerase activity depending on pH.

In addition, the effect of pH on enzyme activity is described with reference to FIG. 8. As pH increases, C4-epimerase activity tends to increases. An appropriate pH range may be dependent on buffers used in enzyme reaction. For example, an appropriate pH for phosphate buffer may range from pH 5 to pH 9, and an appropriate pH for Tris buffer may range from pH 8.0 to pH 8.5. Considering the subsequent processes, pH of 8 or less is suitable.

Figure 9:
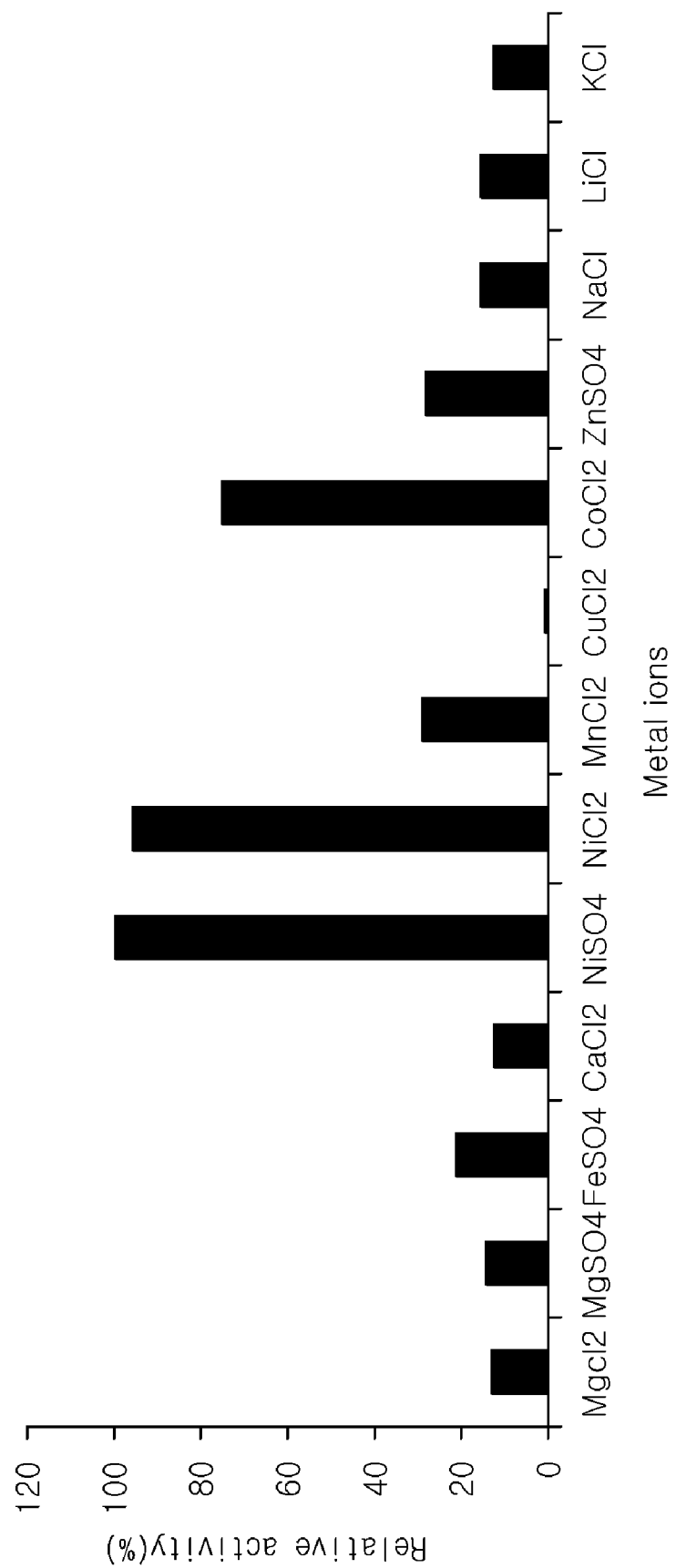
FIG. 9 is a graph depicting C4-epimerase activity depending on the kind of metal salt.

In one embodiment, epimerization using the C4-epimerase may be performed in the presence of a metal salt. The metal salt can act as a catalyst in epimerization. Examples of the metal salt may include $NiSO_4$, $NiCl_2$, $CoCl_2$, $MnCl_2$, or $ZnSO_4$. Specifically, at least one of $NiSO_4$, $NiCl_2$ or $CoCl_2$ may be used. Referring to FIG. 9, C4-epimerase activity may vary depending on the kind of metal salt. Here, $NiSO_4$, $NiCl_2$, $CoCl_2$, $MnCl_2$, and $ZnSO_4$ are referred in descending order of C4-epimerase activity. The concentration of the metal salt may range from 0.001 mM to 50 mM. Specifically, the concentration of the metal salt may range from 0.01 mM to 25 mM.

The epimerized product may include tagatose in an amount of 0.05% by weight (wt %) or more, for example, 0.07 wt % or more, specifically, 0.1 wt % or more. The conversion rate of tagatose may be 5% or more, for example, 7% or more.

In the present invention, any purification methods known in the art may be used. Examples of the purification method may include ion purification, and chromatography or crystallization, without being limited thereto. Separation of sugars by a chromatographic method may be performed based on difference in weak bonding strengths between sugars to be separated and metal ions attached to ion resins. In one embodiment, the ion resins may be strong acidic cation exchange resins to which a residue of K, Na, Ca, or Mg is attached.

In the case where sugars to be separated are ketohexoses such as fructose and tagatose, separate resins having residues such as K, Na, and the like is used due to structural similarity. This means that pure tagatose can be separated only when two separate chromatographic methods are performed in sequence. Examples of metal ion residues used in chromatographic separation may include K, Na, Ca, and Mg, without being limited thereto.

The chromatography is specifically SMB (Simulated Moving Bed) chromatography.

In one embodiment, before or after purification, decoloring, desalting or both decoloring and desalting may further be performed. Specifically, before purification, decoloring, desalting or both decoloring and desalting may be performed. Decoloring may include adding activated carbon with stirring in an amount of 0.05 wt % to 5.0 wt % in the epimerized product. Stirring may be carried out at a stirring speed of 10 ppm to 1000 rpm, specifically 10 ppm to 100 ppm for 30 minutes to 3 hours.

Desalting may be carried out using a cation exchange resin, an anion exchange resin or both the cation and anion exchange resin. Through the decoloring and ion purification processes, it is possible to remove impurities such as coloring materials and ionic materials in the epimerized product.

The cation exchange resin is a polymer having acidic groups and capable of exchanging cations such as hydrogen ions or metal ions. The anion exchange resin is a polymer having basic groups and capable of exchanging ammonium groups with anions such as hydroxyl ions or halide ions. In the present invention, at least one of the cation exchange resins and the anion exchange resins may be used. The cation exchange resins and the anion exchange resins may be used simultaneously in order to effectively remove ionic materials. In this case, the ratio of the cation exchange resins to the anion exchange resins may be 1:1 to 1:3, specifically 1:1.5 to 1:2. After ion purification, the content of ionic materials in the epimerized product may be 10 microsiemens or less per unit centimeter in measurement using an electric conducting system.

The epimerized product having passed through the purification, decoloring and/or desalting processes such that tagatose is separated and impurities such as coloring materials and ionic materials are removed is further concentrated to be used in subsequent reaction. For example, the epimerized product may be concentrated to have a concentration of tagatose of 40 Bx or more or 50 Bx or more.

The purified epimerized product may be crystallized by slowly cooling the epimerized product. Crystallization may be performed by cooling the epimerized product from 40° C. to 90° C. at a rate of 0.1° C. to 5° C. per hour. The obtained tagatose crystals may be subjected to dehydration and drying.

Figure 2:
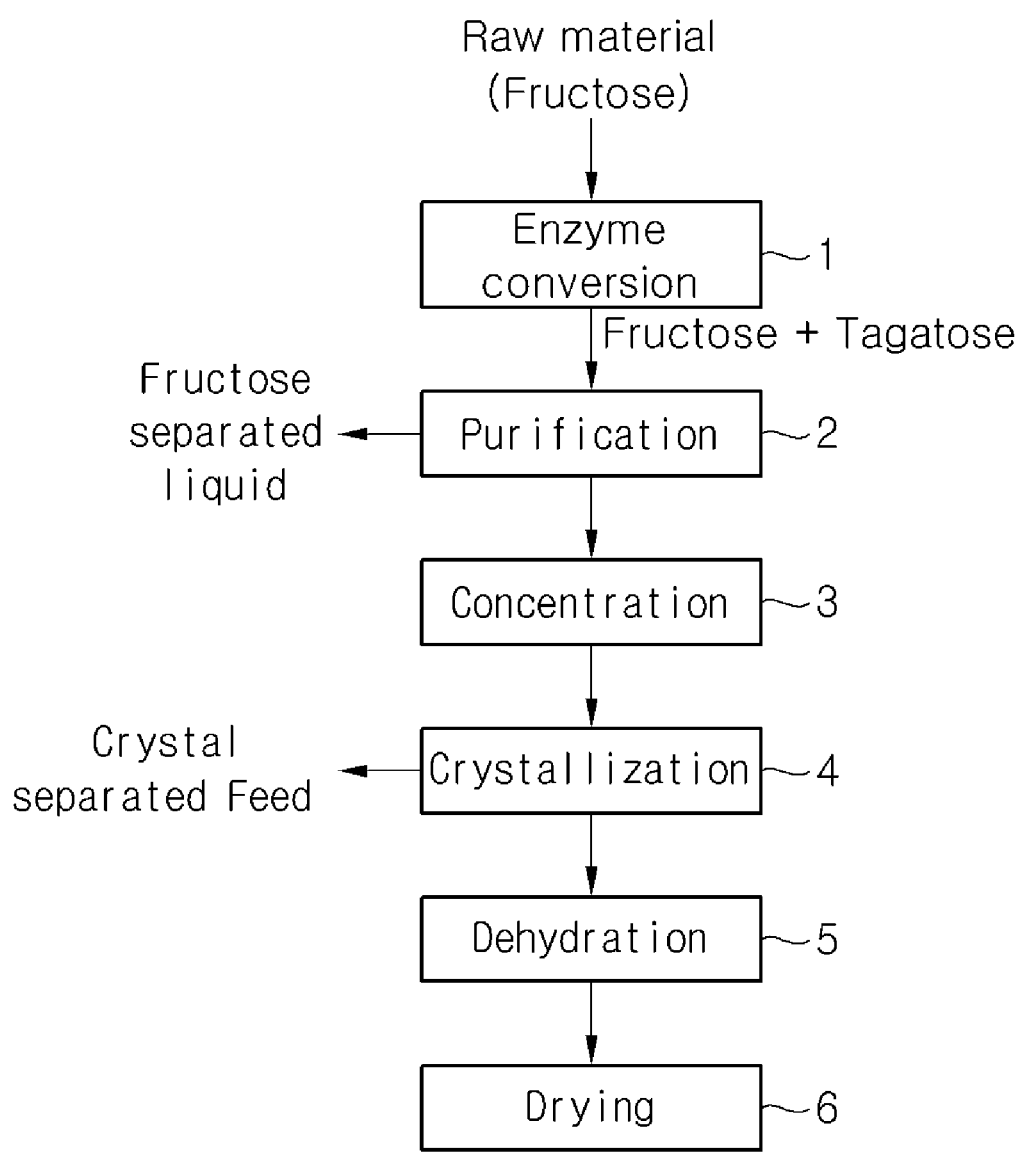
FIGS. 2 to 5 show flowcharts of processes of producing tagatose in accordance with embodiments of the present invention.

Referring to FIG. 2, a method for producing tagatose includes performing epimerization of fructose using hexuronate C4-epimerase to obtain an epimerized product including tagatose; purifying the epimerized product; concentrating the purified epimerized product; crystallizing the concentrated epimerized product to obtain tagatose crystals; and then dehydrating and drying the tagatose crystals.

Tagatose produced by the production method according to one embodiment may have a purity of 80% or more, for example, 90% or more, specifically 95% or more, more specifically 98% or more. The purity may be measured after step b) and before step c). In a further embodiment, the purity may be measured after step c).

According to a further embodiment of the invention, unreacted fructose after step b) may be recycled in step a), or the feed from which crystals are separated after step c) may be recycled in step b), or both processes may be performed.

Figure 3:
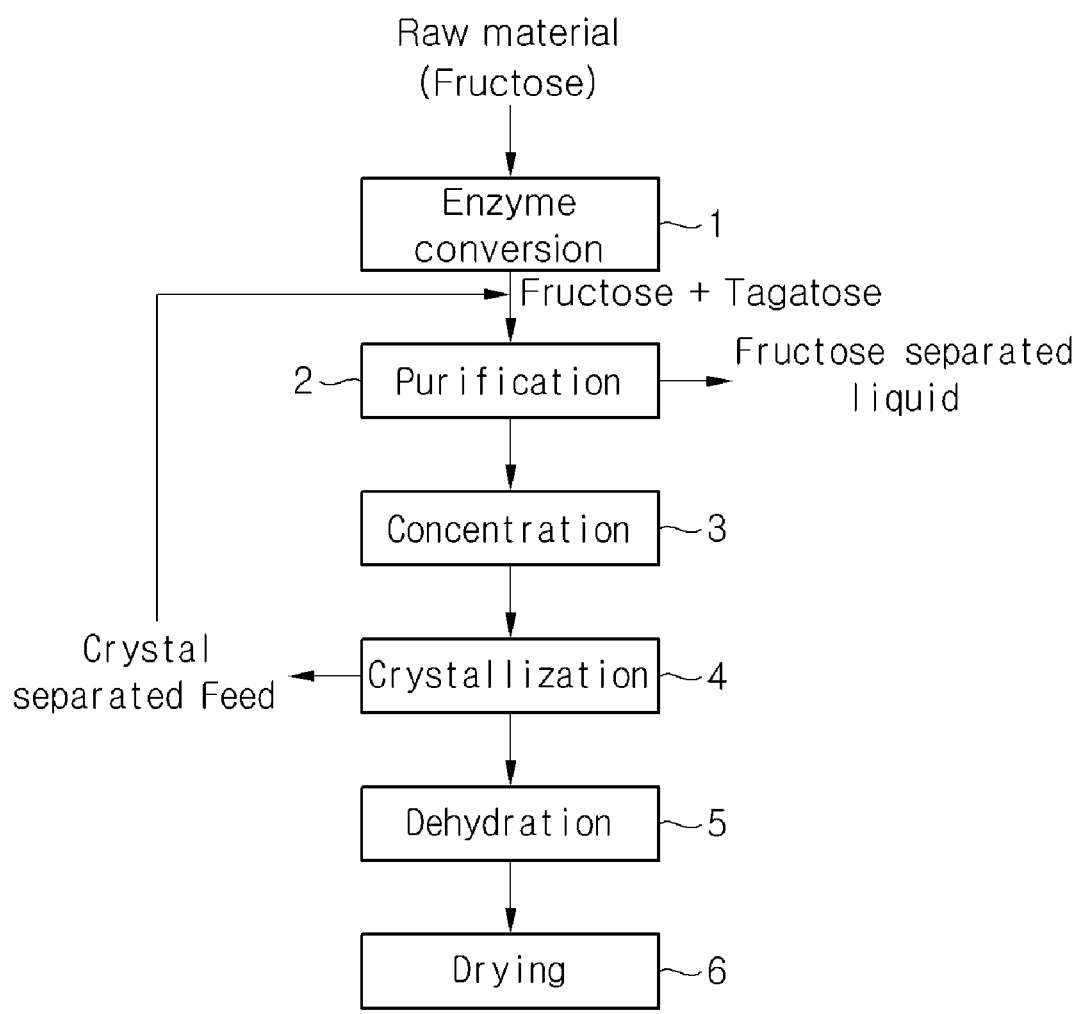
Figure 4:
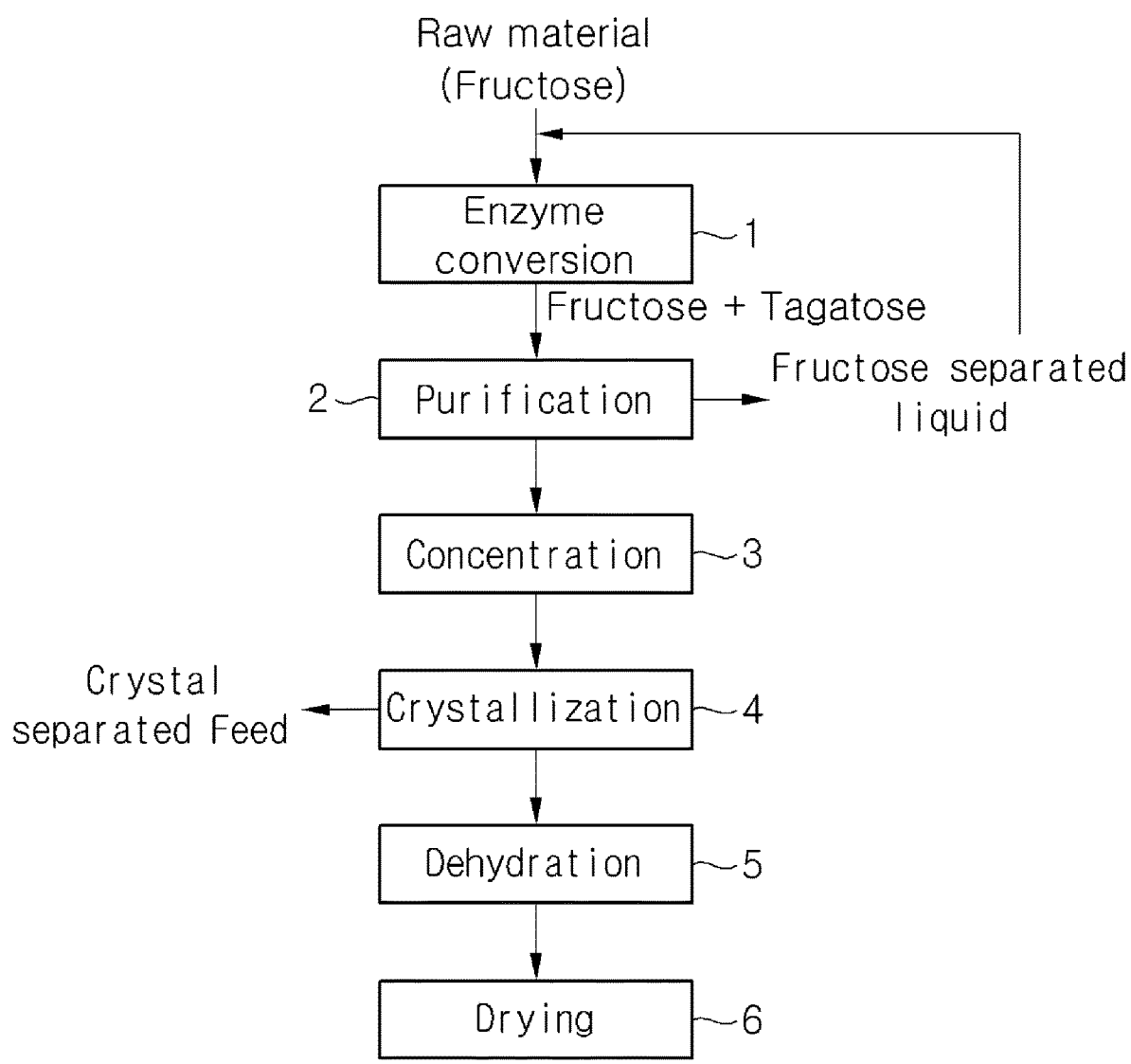
Figure 5:
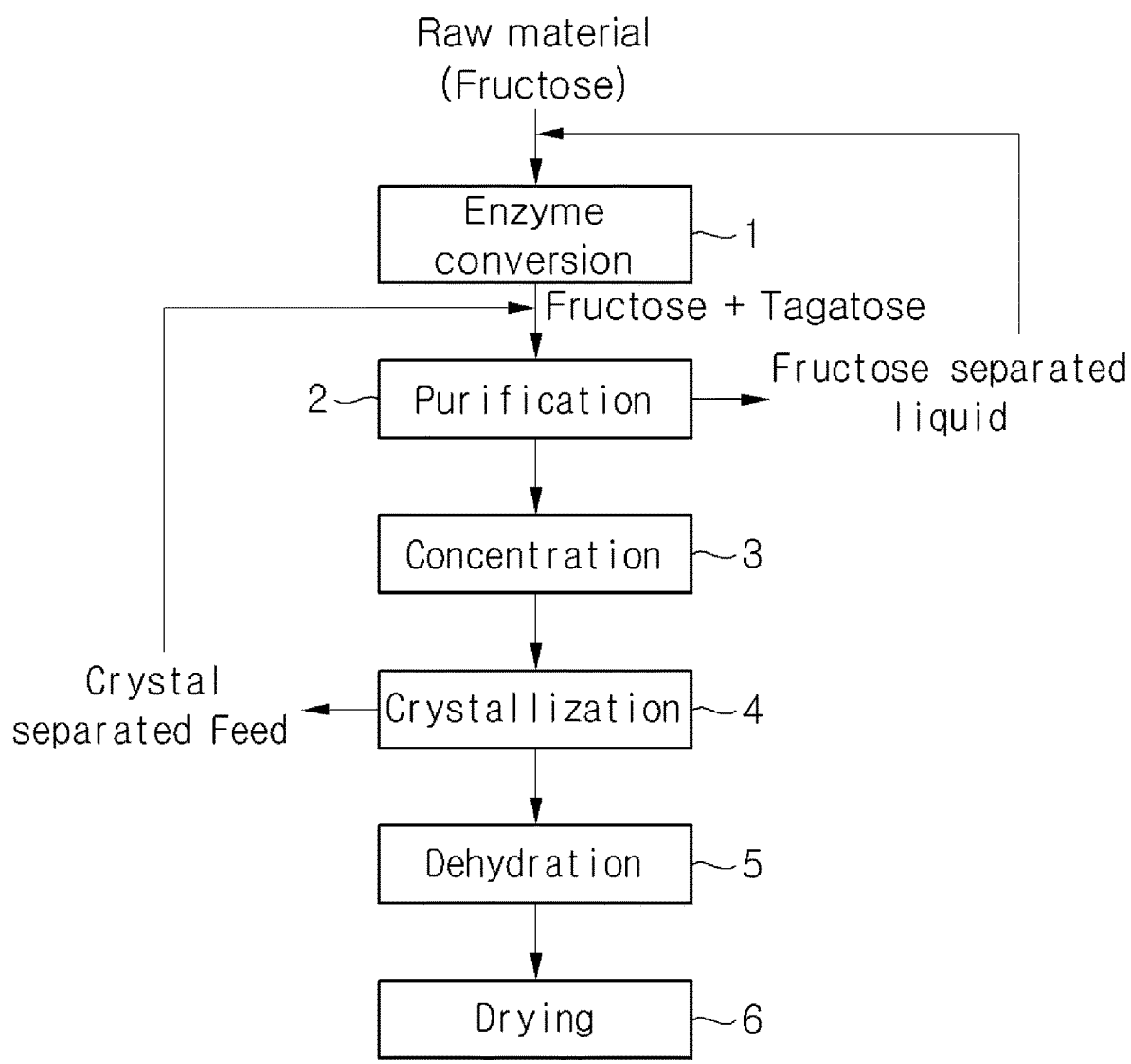

Referring to FIG. 4, tagatose and fructose in the epimerized product are separated through the purification step, and the separated fructose may be reused as a substrate for epimerization in step a). In addition, referring to FIG. 3, tagatose in crystal form and the feed from which crystals are removed are separated in the crystallization step. The feed may include a certain amount of tagatose, which is reused in the purification step. FIG. 5 depicts one embodiment of the present invention wherein reuse of the separated fructose in step a) and reuse of the feed from which crystals are removed in step b) are performed at the same time.

The sugar solution obtained from hydrolysis of sucrose, isomerization of glucose and/or hexuronate C4-epimerization according to one embodiment of the invention may be a mixed sugar solution containing at least one selected from the group consisting of sucrose, glucose, fructose and tagatose. The sugar solution may be separated using a chromatographic separation method.

In general, the mixed sugar comprised of the aldohexose and the ketohexose can be economically separated by chromatography using a resin having cation residues. However, when the mixed sugar comprised of the same kind of sugar, a resin for separation having residues such as K and Na is used due to structural similarity. This means that pure tagatose can be obtained only by sequentially performing two different chromatography processes. Examples of metal ion residues usable in chromatographic separation may include K, Na, Ca, and Mg, without being limited thereto.

Chromatography is preferably SMB (Simulated Moving Bed) chromatography. Unreacted reactants in the chromatographic separation step may be optionally recycled depending on the kind of sugar solution as below.

When the sugar solution contains tagatose as a main component (90% or more), tagatose may be concentrated and crystallized, as needed.

When the sugar solution contains fructose as a main component, the sugar solution may be concentrated and recycled to a step prior to the epimerization step.

When the sugar solution contains glucose as a main component, the sugar solution may be concentrated and recycled to a step prior to the isomerization step.

When the sugar solution contains sucrose as a main component, the sugar solution may be concentrated or crystallized, and then processed, which is used as a sucrose solution or as other raw materials.

EXAMPLES

Hereinafter, the present invention will be described in more detail with reference to the following examples. It should be understood that these examples are provided for illustrative purposes only and are not to be in any way construed as limiting the present invention.

Example 1

Evaluation of Chromatographic Separation Characteristics According to Enzyme Conversion Rate In order to separate and crystallize a target material (tagatose) with high purity from a mixed sugar (fructose and tagatose), purification using chromatographic separation is very important. In general, purification of sugar solution for obtaining crystallized products achieves different recovery yield (%), depending on the content of the target material (tagatose). High recovery yield (%) is obtained in proportion with increase in the content of the target material. As a result, it is possible to produce a final product with relatively low production and processing cost. In order to effectively produce crystal sugars (high purity, high yield), it is very important to ensure that the target material (tagatose) contained in the feed has a purity of 90% or more, more preferably 95%.

The operational conditions for chromatography may cause various results depending on feed content, the kind of separation resin, desired yield or purity of a target material (tagatose) in the separated liquid. Accordingly, the feed content of the reaction solution obtained through the enzymatic conversion process of converting fructose into tagatose, namely, the conversion rate (%) of fructose to tagatose, affects yield of chromatography. When the purity of tagatose in the separated liquid was fixed to 95%, which was preferable in the crystallization process, changes in yield (%) of chromatographic separation depending on the feed content (%) of fructose and tagatose in the feed were observed.

In order to maximize efficiency of chromatographic separation of sugars, partially improved results were obtained by changing the size of resins used in the chromatographic separation, the kind of modified metal ion residue (for example K, Na, Ca, Mg, and the like). However, in the present invention, a separation resin having modified Ca residues was used in consideration of general separation characteristics of fructose and tagatose. Table 1 shows conditions for evaluation.

TABLE 1

| Sample | Mixed monosaccharide sample consisting of fructose and tagatose |
|---|---|
| Concentration of supplied sample | Bx, 60% |
| Adsorbent | Amberlite (Amberlite CR-1310; Ca-type) |
| Column size | 20 mm × 1000 mm (314 ml) |
| Desorbent | H2O |
| Volume supplied | 15 ml |
| Flow rate | 26 ml/min (LV 5 m/h) |
| Temperature | 60° C. |

Under the aforementioned conditions, results of the SMB chromatographic separation test depending on the feed content (%) of fructose and tagatose are shown in the following Table. When the purity of tagatose in the separated liquid was fixed to 95%, which was preferable in the crystallization process, recovery yield of tagatose and fructose depending on the feed content of fructose and tagatose was observed. The results are shown in Table 2.

TABLE 2

Analysis results of chromatographic separation characteristics depending on feed content of fructose and tagatose

| | | Sample 1 | Sample 2 | Sample 3 | Sample 4 | Sample 5 | Sample 6 | Sample 7 |
|---|---|---|---|---|---|---|---|---|
| Feed content (%) | Tagatose | 5 | 10 | 15 | 20 | 25 | 30 | 35 |
| | Fructose | 95 | 90 | 85 | 80 | 75 | 70 | 65 |
| Recovery yield (%) | Tagatose | 82.14 | 86.15 | 90.98 | 92.16 | 94.13 | 94.45 | 95.48 |
| | Fructose | 99.99 | 99.56 | 99.44 | 99.02 | 98.49 | 98.12 | 97.53 |
| Tagatose Purity (%) | | 95.46 | 95.76 | 95.85 | 95.63 | 95.39 | 95.48 | 95.62 |

Figure 11:
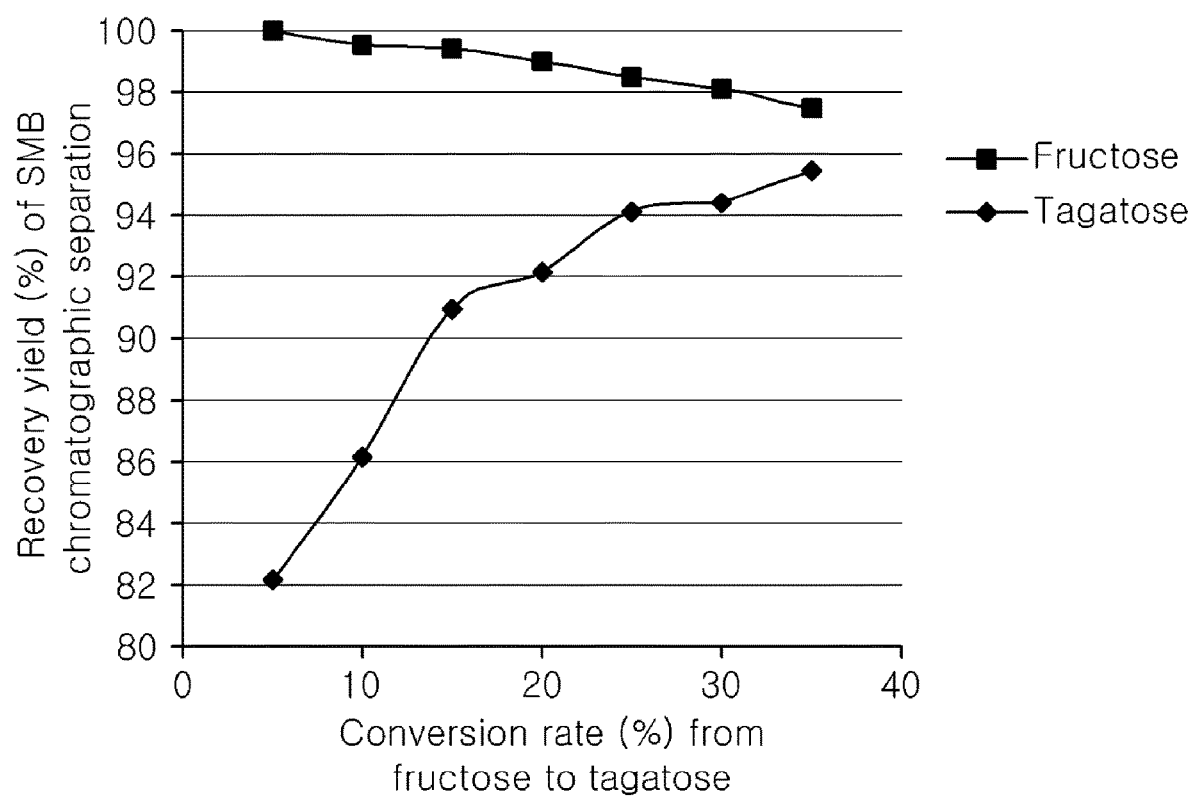
FIG. 11 shows graphs depicting a relationship between a conversion rate and a recovery yield for fructose and tagatose.

Referring to Table 2 and FIG. 11, it can be seen that recovery yield (%) of tagatose is especially affective to enzyme conversion rate (%) as compared with fructose. In order to produce tagatose at a recovery yield of 90% or more and a purity of 95%, the enzyme titer and process conditions should be established such that enzyme conversion rate (%) of 15% or more can be obtained. Likewise, in order to produce tagatose at a recovery yield of 85% or more and a purity of 95%, enzyme conversion rate (%) of 10% or more should be ensured. Thus, it can be confirmed that enzyme conversion rate (%) is a very important factor in terms of efficiency of the production process according to the present invention.

Example 2

Preparation of Ketohexose C4-Epimerase

Polymer chain reactions (PCRs) were performed using, as a template, a genomic DNA (SEQ ID NO: 1) of *Thermotoga maritima* (strain ATCC 43589/MSB8/DSM 3109/JCM 10099), a heat resistant microorganism, and adding a forward primer (5'-GGGCATATGATGGTCTTGAAAGTGTTCAAAG-3'; SEQ ID NO: 5) and a reverse primer (5'-AAACTCGAGCCCCTCCAGCAGATCCACGTG-3'; SEQ ID NO: 6).

Further, polymerase chain reactions (PCR) were performed by using, as a template, a genomic DNA (SEQ ID NO: 2) of *Thermotoga neapolitana* (DSM 4359), a heat resistant microorganism, and adding a forward primer (5'-GGGCATATGATGGTCTTGAAAGTGTTCAAAG-3'; SEQ ID NO: 5) and a reverse primer (5'-AAACTCGAGTCACCCCTTCAACAGGTCTACGTG-3'; SEQ ID NO: 7).

The conditions for PCRs are shown in Tables 3 and 4. The genes amplified by PCR were inserted into a pET-21a vector, followed by transforming into *E. coli* DH5α strain. From the transformed strain, plasmids were isolated, which were sequenced to identify the base sequences of the inserted genes. The plasmids were transformed into a protein expression strain, *E. coli* BL21(DE3), which was used in the production of ketohexose C4-epimerase. In order to produce ketohexose C4-epimerase, *E. coli* BL21(DE3)pET21a-TM (including a *Thermotoga maritima*-derived enzyme expression gene) and *E. coli* BL21(DE3) pET21a-TN (including a *Thermotoga neapolitana*-derived enzyme expression gene) were cultured in an LB medium including 100 μg/ml of ampicillin for around 2 hours, wherein the cultivation temperature was 37° C. and the stirring speed was 180 rpm. After cultivation, optical density of the microorganisms at 600 nm was measured. If the optical density value falls within from 0.4 to 0.8, 0.25 mM of isopropyl β-D-1-thiogalactopyranoside (IPTG) was added, followed by culturing overnight under the same conditions to induce protein expression.

TABLE 3

| Composition of reaction solution | Amount added (μl) |
|---|---|
| PCR buffer (5X) | 10 |
| dNTPs (2.5 mM each) | 1 |
| PCR template (*T. maritime* gDNA) | 1 |
| Forward primer (100 pmol) | 1 |
| Reverse primer (100 pmol) | 1 |
| DNA polymerase (Phusion, NEB Co. Ltd.) | 0.5 |
| Sterilized distilled water | 35.5 |

TABLE 4

| Step | Temperature (° C.) | Time (sec) | Cycle |
|---|---|---|---|
| Initial Denaturation | 98 | 30 | 1 |
| Denaturation | 98 | 10 | 35 |
| Annealing | 65.7 | 30 | |
| Extension | 72 | 50 | |
| Final Extension | 72 | 350 | 1 |

Example 3

Purification of Ketohexose C4-Epimerase

In order to measure activity of ketohexose C4-epimerase expressed in the microorganism, protein purification was carried out by the following method. A culture solution in which protein expression was completed was centrifuged at 8,000 rpm for 10 minutes to collect cultured cells, which were re-suspended in a 50 mM $NaH_2PO_4$ (pH 8.0) buffer including 10 mM of imidazole and 300 mM of NaCl. The suspended cells were disrupted by a sonicator and centrifuged at 13,000 rpm for 10 minutes to harvest a supernatant. The harvested supernatant was flowed through a column packed with a Ni-NTA resin. To this, 50 mM $NaH_2PO_4$ (pH8.0) buffer including 20 mM of imidazole and 300 mM of NaCl was flowed through in an amount 10 times the volume of the resin in the column, thereby removing proteins attached non-specifically to the resin. Finally, 50 mM $NaH_2PO_4$ (pH 8.0) buffer including 250 mM of imidazole and 300 mM of NaCl was flowed through to elute and purify a ketohexose C4-epimerase. In order to remove imidazole in the purified enzyme, 50 mM $NaH_2PO_4$ (pH 8.0) buffer was flowed several times such that the concentration of imidazole was 0.01 mM or less. The purified enzyme was quantified by Bradford assay.

Example 4

Conversion from Fructose into Tagatose

In order to measure activity of enzymes obtained in Examples 2 and 3, the purified enzyme was added to 1 wt % of fructose, 0.01 mM $ZnSO_4$, and 50 mM phosphate buffer (pH 7.0), followed by reacting at a reaction temperature of 60° C. for 3 hours. The concentration of tagatose converted by ketohexose C4-epimerase and the conversion rate from fructose to tagatose are shown in Table 5.

Figure 6:
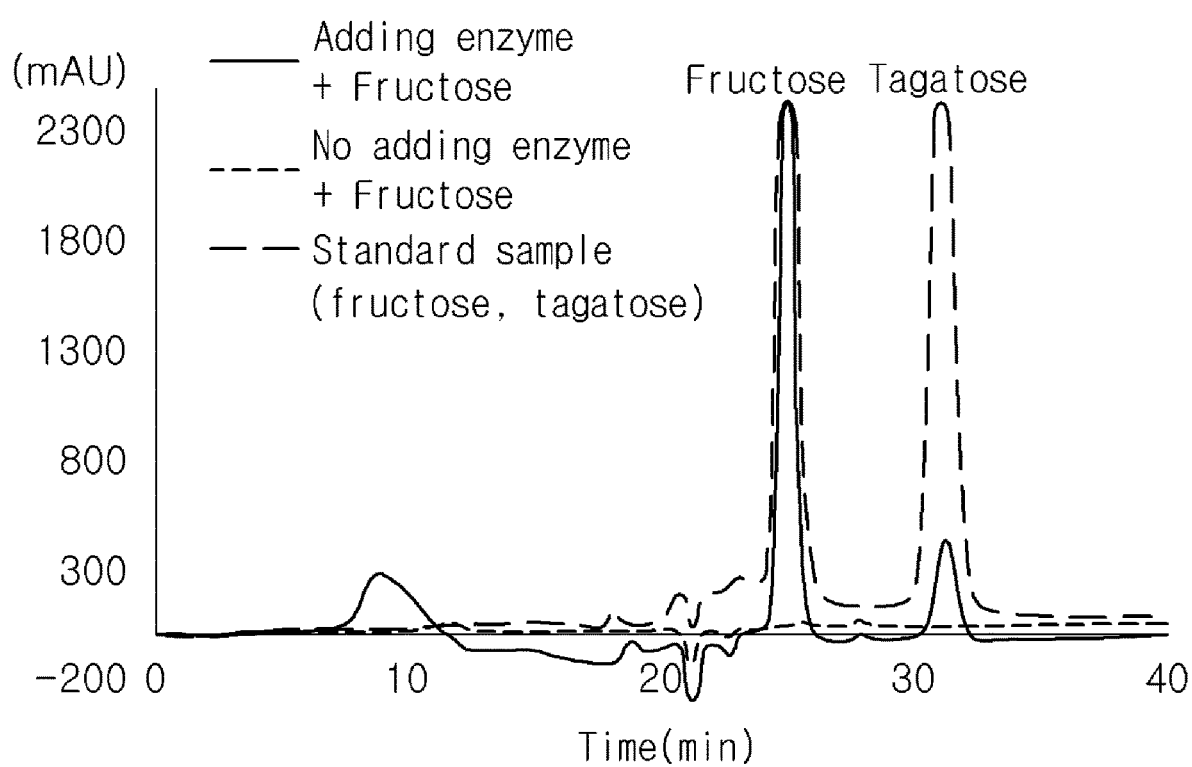
FIG. 6 is an HPLC graph depicting production of tagatose through C4-epimerization using fructose as a substrate.

Further, after reaction, the remaining fructose and tagatose as products were quantified by HPLC, wherein the column was Shodex Sugar SP0810, the column temperature was 80° C., and water as a mobile phase was flowed through at a rate of 0.5 ml/min. FIG. 6 depicts the results of enzyme reaction using fructose as a substrate by detecting and quantifying peaks by HPLC.

TABLE 5

|  | Tagatose concentration (%) | Conversion rate (%) |
|---|---|---|
| T. maritima | 0.093 | 9.3 |
| T. neapolitana | 0.080 | 8.0 |

Referring to Table 5 and FIG. 6, it was identified that peaks for fructose and tagatose were not observed when the conversion was performed by adding only enzymes to the phosphate buffer without adding fructose (represented by a dashed line).

However, when fructose and enzymes were added in order to perform epimerization (represented by a solid line), only the peak for fructose was observed prior to 30 minutes after the start of the enzyme reaction. As time passed, peaks for tagatose were observed after about 30 minutes from the start of the enzyme reaction.

From the results shown in Table 5 and FIG. 6, it was confirmed that fructose could be converted into tagatose using the enzymes prepared in Examples 2 and 3.

Example 5

Construction of Mutant Library and Selection of Improved Mutant

A *T. neapolitana*-derived gene was used as a template to perform a random mutation. Specifically, *T. neapolitana* was subjected to random mutagenesis using a Diversify Random Mutagenesis Kit (manufactured by ClonTech Co., Ltd.). The resultant gene was amplified through PCR under the conditions listed in the following Tables 6 and 7. The amplified gene was inserted to a pET-28a vector to transform *E. coli* BL21(DE3) strain. The remaining steps were performed in the same manner as in Example 2.

TABLE 6

| Composition of reaction solution | Amount added(μl) |
|---|---|
| PCR Grade Water | 36 |
| 10X TITANIUM Taq Buffer | 5 |
| MnSO4 (8 mM) | 4 |
| dGTP (2 mM) | 1 |
| 50X Diversify dNTP Mix | 1 |
| Primer mix | 1 |
| Template DNA | 1 |
| TITANIUM Taq Polymerase | 1 |

TABLE 7

| Step | Temperature (° C.) | Time (sec) | Cycle |
|---|---|---|---|
| Initial Denaturation | 94 | 30 | 1 |
| Denaturation | 94 | 30 | 25 |
| Annealing/Extension | 68 | 60 |  |
| Final Extension | 68 | 60 | 1 |

A high activity candidate mutant was selected from mutant libraries obtained through random mutagenesis and mutated portions in the base sequence of the mutants were identified by DNA sequencing. The mutant was found to have a total of 5 mutated positions in the amino acid sequence (5125D/V163A/D186N/F2631/D311G).

The mutant has a genomic DNA base sequence represented in SEQ ID NO: 3 and the amino acid sequence encoding the enzyme produced by the mutant was as set forth in SEQ ID NO: 4. The mutant producing ketohexose C4-epimerase is *E. coli* BL21(DE3) pET28a-TN(m) (accession number: KCCM11544P). The mutant was used to produce C4-epimerase in the same manner as in Examples 2 and 3.

Example 6

Evaluation of Conversion Rate of Fructose to Tagatose Using Improved Mutant

Using the improved mutant-derived enzyme, the conversion rates depending on temperature, pH, and metal salt were evaluated by the following method.

(1) Comparison Evaluation of Enzyme Activity Depending on Reaction Temperature

Figure 7:
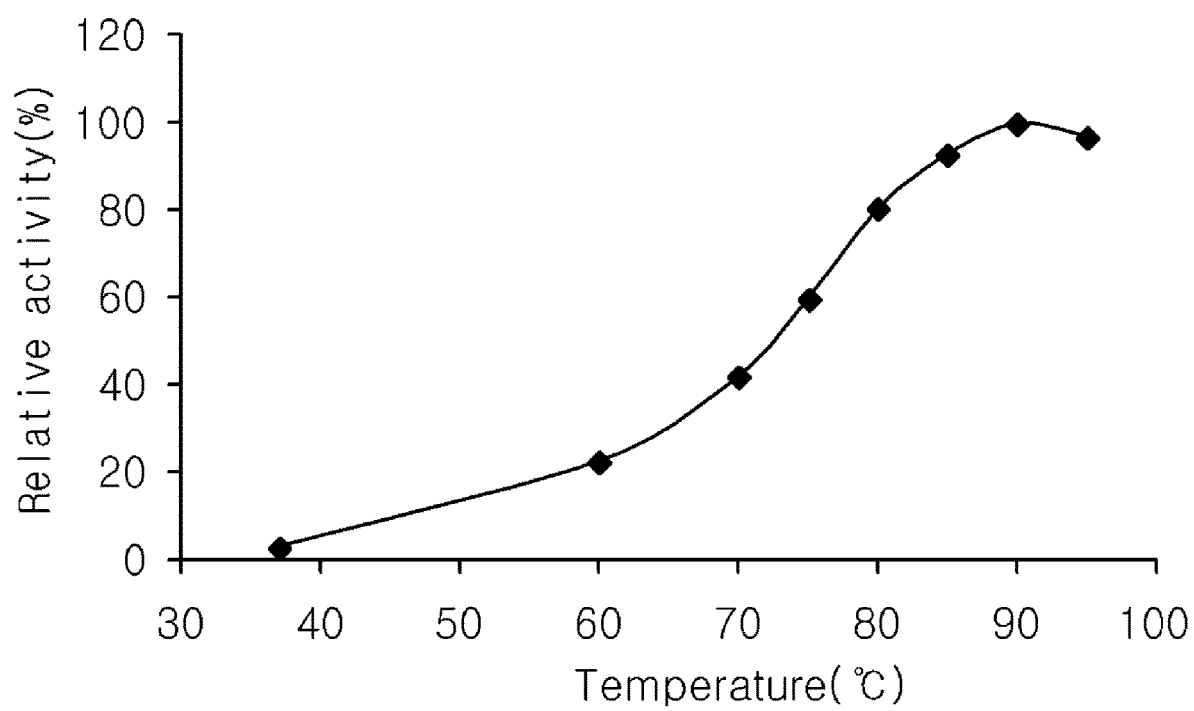
FIG. 7 is a graph depicting C4-epimerase activity depending on reaction temperature.

In order identify a change in enzyme activity depending on reaction temperature, the purified enzyme obtained in Example 5 was added to 10 wt % of fructose, 0.3 mM $ZnSO_4$, and 50 mM phosphate buffer (pH 7.0), and then reacted for 3 hours. As shown in FIG. 7, enzyme activity was measured at different reaction temperatures from 37° C. to 96° C.

Enzyme activity showed a tendency of increasing with increasing temperature. However, enzyme activity decreased at a reaction temperature of 90° C. or more.

(2) Comparison Evaluation of Enzyme Activity Depending on Reaction pH

In order identify a change in enzyme activity depending on reaction pH, the purified enzyme obtained in Example 5 was added to 10 wt % of fructose, 0.01 mM $NiSO_4$, a phosphate buffer or Tris buffer, and reacted for 3 hours. Specifically, a potassium phosphate buffer was used at pH 5 to pH 8.0, and a Tris buffer was used at pH 8.0 to pH 8.5. As shown in FIG. 8, enzyme activity was measured at different reaction pH. When the potassium phosphate buffer was used and when the Tris buffer was used, enzyme activity showed a tendency of increasing with increasing pH. At the same pH, decline in enzyme activity was observed when the Tris buffer was used.

(3) Comparison Evaluation of Enzyme Activity Depending on the Kind of Metal Salt In order identify a change in enzyme activity depending on the kind of metal salt, the purified enzyme obtained in Example 5 was added to 10 wt % of fructose, and 50 mM phosphate buffer, and reacted for 3 hours. In this reaction, 1 mM of 13 different metal salts was used. As a result, the metal salts showed different enzyme activity in the order of $NiSO_4 > NiCl_2 > CoCl_2 > MnCl_2 = ZnSO_4$ upon listing metal salts in descending order of activity (see FIG. 9).

(4) Evaluation of Conversion Rate by Enzyme Reaction

Figure 10:
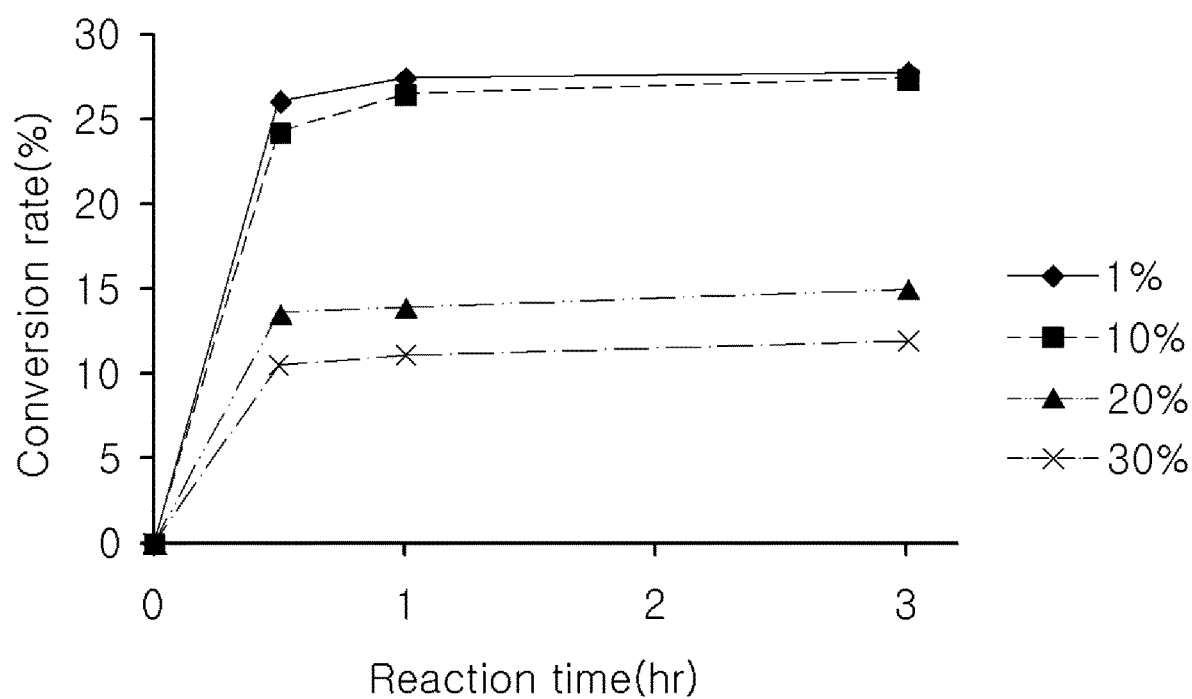
FIG. 10 is a graph depicting a conversion rate from fructose to tagatose depending on concentration of fructose as a substrate.

In order identify a change in enzyme activity depending on substrate concentration, the purified enzyme obtained in Example 5 was added to 10 wt % of fructose, 0.3 mM $NiSO_4$, and 50 mM phosphate buffer, and then reacted at 60° C. for 3 hours. In order to evaluate the conversion rate, enzyme reaction was performed for 18 hours. Referring to FIG. 10, it can be seen that the conversion rate from fructose to tagatose was 30% when the improved enzyme mutant was used.

Example 7

Chromatographic Separation of Fructose and Tagatose

The purified enzyme obtained in Example 5 was added to 10 wt % of fructose, 0.01 mM $NiSO_4$, and 50 mM phosphate buffer, and then reacted at 60° C. for 3 hours. The obtained tagatose mixed solution was added to 0.1 to 0.5% (wt/v) of activated carbon powder, followed by stirring at 10 rpm to 100 rpm for 0.5 hour to 1 hour, filtered by a filter press to remove colored materials, thereby obtaining a mixed solution of fructose and tagatose.

In order to effectively separate fructose and tagatose from the mixed solution of fructose and tagatose by chromatography, the mixed solution was flowed through columns packed with a cation exchange resin substituted with hydrogen groups and an anion exchange resin substituted with hydroxyl groups, thereby removing ion components in the solution.

By the aforementioned decoloring and desalting processes, a mixed solution of tagatose produced from fructose, from which impurities such as colored materials and ion components were removed, was obtained. The mixed solution was concentrated to 60% (g/g solution) and then subjected to fractional chromatography using an Advanced Simulated Moving-bed System (manufactured by Organo in Japan) packed with a strong acidic cation exchange resin substituted with calcium groups (Amberlite CR1310 Ca), thereby measuring purity of the components, recovery yield and a ratio between a mixed feed of tagatose converted from fructose and water as a mobile phase (volume ratio of desorbent/feed).

TABLE 8

| Condition | Result |
| --- | --- |
| Ratio of mixed feed of tagatose converted from fructose (%) | fructose 75.4%, tagatose 24.6% |
| Volume ratio of Desorbent/Feed | 2.96 |
| Purity of tagatose (%) | 99.1 |
| Recovery yield of tagatose (%) | 94.4 |
| Purity of fructose (%) | 92.9 |
| Recovery yield of fructose (%) | 99.6 |

Example 8

Crystallization of Tagatose

The solution collected from chromatographic separation of Example 7 was subjected to crystallization. Crystallization was performed by heat concentrating the solution under vacuum such that tagatose concentration became 70 Bx, followed by slowly cooling from 60° C. to 30° C. at a rate of 0.7° C. to 1° C. per hour.

After crystallization, the resultant crystals were subjected to centrifugal dehydration to harvest crystals. The crystals were dried at 60° C. using a fluid bed dryer for 1 hour to measure purity and recovery yield of crystals.

TABLE 9

Summary of crystallization results

| Condition | Result |
| --- | --- |
| Purity of tagatose crystals (%) | 99.9 |
| Recovery yield of tagatose crystals (%) | 40.2 |

Example 9

Design of Continuous Recycling Process

A continuous recycling production process of tagatose using the purified enzyme obtained in Example 5 was designed as follows.

The continuous recycling production process is briefly shown in FIGS. 2, 3, 4, and 5. In the purification step, processes for improving product quality such as decoloring, and desalting can be optionally performed as needed.

The continuous recycling production process includes passing a solution containing fructose as a main component through a hexuronate C4-epimerase reactor to produce tagatose; subjecting the epimerization product comprised of a mixed sugar of fructose and tagatose to chromatographic separation; optionally, performing a concentration step depending on tagatose concentration in the purified epimerized product; concentrating the chromatographic separation solution containing tagatose as a main component (90% or more); and if necessary, performing crystallization to produce tagatose. The remaining chromatographic liquid containing fructose as a main component was recycled to the prior step to the epimerization reactor and/or the non-crystallized feed obtained in crystallization of tagatose was recycled to the step subsequent to epimerization.

The invention claimed is:

1. A method for producing tagatose, comprising:
   a) performing epimerization of fructose using an enzyme to obtain an epimerized product comprising tagatose, wherein the enzyme comprises the amino acid sequence of SEQ ID NO: 4 or an amino acid sequence encoded by the nucleic acid sequence of SEQ ID NO: 1, 2 or 3; and
   b) purifying the epimerized product.

2. The method for producing tagatose according to claim 1, wherein the enzyme is derived from *Thermotoga maritima* or *Thermotoga neapolitana*.

3. The method for producing tagatose according to claim 1, wherein the epimerization step comprises reacting fructose and enzyme at a temperature ranging from 60° C. to 90° C. and pH 5 to 8.

4. The method for producing tagatose according to claim 3, wherein the epimerization step is performed in the presence of a metal salt.

5. The method for producing tagatose according to claim 4, wherein the metal salt comprises at least one of $NiSO_4$, $NiCl_2$, $CoCl_2$, $MnCl_2$, and $ZnSO_4$.

6. The method for producing tagatose according to claim 1, wherein a rate of epimerization for converting fructose to tagatose is 5% or higher.

7. The method for producing tagatose according to claim 1, wherein fructose is produced by hydrolysis of sucrose or isomerization of glucose.

8. The method for producing tagatose according to claim 1, wherein the purification step is performed by at least one of chromatography, fractional crystallization, and ion purification.

9. The method for producing tagatose according to claim 8, wherein decoloring, desalting or both decoloring and desalting are performed before or after the purification step.

10. The method for producing tagatose according to claim 1, further comprising crystallizing the purified epimerized product, after the purification step, wherein the purified epimerized product is concentrated before the crystallization step.

11. The method for producing tagatose according to claim 1, further comprising crystallizing the purified epimerized product, after the purification step, wherein, after step b), unreacted fructose is recycled to step a), or after the crystallization step, feed from which crystals are separated is recycled to step b), or both steps are performed.

12. The method for producing tagatose according to claim 2, further comprising crystallizing the purified epimerized product, after the purification step, wherein, after step b), unreacted fructose is recycled to step a), or after the crystallization step, feed from which crystals are separated is recycled to step b), or both steps are performed.

13. The method for producing tagatose according to claim 3, further comprising crystallizing the purified epimerized product, after the purification step, wherein, after step b), unreacted fructose is recycled to step a), or after the crystallization step, feed from which crystals are separated is recycled to step b), or both steps are performed.

14. The method for producing tagatose according to claim 1, further comprising crystallizing the purified epimerized product, after the purification step.

\* \* \* \* \*

SEQUENCE LISTING

<160> NUMBER OF SEQ ID NOS: 7

<210> SEQ ID NO 1
<211> LENGTH: 1446
<212> TYPE: DNA
<213> ORGANISM: Thermotoga maritima
<220> FEATURE:
<223> OTHER INFORMATION: Hexuronate C4-epimerase

<400> SEQUENCE: 1

```
atggtcttga aagtgttcaa agaccacttt ggaagggat  acgaagttta cgaaaagtct    60
tatagagaaa aggattctct ttctttcttc ttgacaaagg aagaggaagg aaaaattctg   120
gtggtggctg agaaaaggc  acctgaaggt ctgtcgtttt tcaaaaaaca gcgggcggag   180
ggtgtttcgt tcttttttctg tgagagaaat catgagaact tggaagttct cagaaaatac  240
tttccagatc tcaaaccagt tcgagcggga ttgagagcgt cttttggaac aggtgacaga   300
ctcggtatca ccacaccggc tcacgtgagg gcgttgaagg attcagggct tttttcccatc  360
tttgcgcagc agtcggtgag ggagaacgag agaacgggaa ggacctggag agatgtgctg   420
gacgatgcca catggggagt tttccaggag ggatacagtg agggattcgg agcggatgca   480
gaccatgtga agcggccgga ggatcttgtt tcggctgcaa gggaaggttt caccatgttc   540
acaatcgatc cttcggatca tgtgaggaat ctttcaaaac ttacagaaaa ggaaagaaat   600
gagaaattcg aagagattct gagaaaggaa aggatcgaca ggatctatct cggtaagaaa   660
tactctgttc tcggtgagaa gatcgaattc gatgagaaga atctcagaga tgcggcgctc   720
gtgtattacg atgcgattgc ccacgtggat atgatgtatc aaattttgaa agacgaaacc   780
ccggatttcg acttcgaagt gtcagttgac gaaacagaaa ctcctacgag tcctctcttc   840
cacattttcg ttgtggaaga actcagacga gaggtgtgg  agttcaccaa tcttgccctg   900
agattcatcg gcgaatggga aagggaata  gattacaagg gggatcttgc acagttcgag   960
agagaaatca aaatgcacgc agaaatcgca aggatgttcg aaggatacaa aatatcactc  1020
cactctggaa gcgacaaatt ttccgtgtat cctgcttttg cttccgcgac aggaggcctt  1080
ttccacgtga agacagccgg aacgagttat cttgaggcgg tgaaggtcat atccatggtc  1140
aacccggagc tcttccggga gatctacagg tgtactctcg atcactttga ggaagacaga  1200
aagtcctatc acatatctgc ggatctgtcg aaagttccgg aagtagagaa agtgaaagat  1260
gaagatcttc caggtctttt tgaagacatc aacgtgagac agttgatcca cgtcacctac  1320
ggctctgttc tgaaagatgc atctttgaaa gaacggctat ttaagacgct tgaacaaaac  1380
gaggaactct tttacgaaac tgtggcaaaa catataaaaa ggcacgtgga tctgctggag  1440
gggtga                                                              1446
```

<210> SEQ ID NO 2
<211> LENGTH: 1446
<212> TYPE: DNA
<213> ORGANISM: Thermotoga neapolitana
<220> FEATURE:
<223> OTHER INFORMATION: Hexuronate C4-epimeras

<400> SEQUENCE: 2

```
atggtcttga aagtgttcaa agatcacttt ggaaggggat acgaagttta cgaaaagtct    60
tatagagaaa aggattctct ctctttcttc ttgacaaagg gagaggaagg aaaaattctg   120
gtagtggctg agaaaaggc  acctgagggt ctgtcgtttt tcaaaaaaca gcgggtggag   180
ggtgtttcgt tcttttttctg tgagagaaat catgagaact tggaagttct cagaaaatac  240
```

```
tttccagatc tcaaaccagt tcgagcggga ttgagagcgt cttttggaac aggtgacaga      300
ctcggtatca ccacaccggc tcacgtgagg gcgttgaagg attcagggct ttttcccatc      360
tttgcgcagc agtcggtgag ggagaacgag agaacgggaa ggacctggag agatgtgctg      420
gacgatgcca catggggagt tttccaggag ggatacagtg agggattcgg agcagacgcc      480
gatcacgtga agcggccgga ggatcttgtt tcggctgcaa gggaaggttt caccatgttc      540
acaatcgatc cttcggatca tgtgaggaat ctttcaaaac tcagtgaaag agaaaagaac      600
gagatgttcg aggaaatact gaaaaagag cgaatcgaca ggatctatct tgggaaaaaa       660
tacaccgtcc tcggtgaaag actggagttc gacgagaaaa atttgaggga tgctgctctg      720
gtgtactatg atgcgatcgc ccacgtggat atgatgtatc aaattttgaa agacgaaacc      780
ccggatttcg acttcgaagt gtcagttgac gaaacagaaa ctcccacgag tcctctcttc      840
cacattttcg ttgtggaaga actcagacga agaggtgtgg agttcaccaa tcttgccctg      900
agattcatcg gcgaatggga aaagggaata gattacaagg gggatcttgc acagttcgag      960
agagaaatca aaatgcacgc agaaatcgca aggatgttcg aaggatacaa aatatcactc     1020
cactctggaa gcgacaaatt ttccgtgtat cctgcttttg cttccgcgac aggaggcctt     1080
ttccacgtga agacagccgg aacgagttat cttgaggcgg tgaaggtcat atccatggtc     1140
aacccggagc tcttccggga gatctacagg tgtgctctcg atcactttga ggaagacaga     1200
aagtcctatc acatatctgc ggatctgtcg aaagttccgg aagtagagaa agtgaaagat     1260
gaagatcttc caggtctttt tgaagacatc aacgtgagac agttgatcca tgtcacctat     1320
ggctctgttc tgaaagatgc atctttgaaa gaacggctgt ttaagacgct tgaacaaaat     1380
gaggaactct tctacgagac cgtggcaaaa catataaaaa ggcacgtaga cctgttgaag     1440
gggtga                                                                1446
```

<210> SEQ ID NO 3
<211> LENGTH: 1473
<212> TYPE: DNA
<213> ORGANISM: Artificial sequence
<220> FEATURE:
<223> OTHER INFORMATION: Hexuronate C4-epimeras

<400> SEQUENCE: 3

```
atggtcttga aagtgttcaa agatcacttt ggaaggggat acgaagttta cgaaaagtct       60
tatagagaaa aggattctct ctctttcttc ttgacaaagg gagaggaagg aaaaattctg      120
gtagtggctg gagaaaaggc acctgagggt ctgtcgtttt tcaaaaaaca gcgggtggag      180
ggtgtttcgt tcttttttctg tgagagaaat catgagaact tggaagttct cagaaaatac     240
tttccagatc tcaaaccagt tcgagcagga ttgagagcgt cttttggaac aggtgacaga      300
ctcggtatca ccacaccggc tcacgtgagg gcgttgaagg attcagggct ttttcccatc      360
tttgcgcagc aggacgtgag ggagaacgaa agaacgggaa ggacctggag agatgtgctg      420
gacgatgcca catggggagt tttccaggag ggatacagtg agggattcgg agcagacgcc      480
gatcacgcga agcggccgga ggatcttgtt tcggctgcaa gggaaggttt caccatgttc      540
acaatcgatc cttcgaatca tgtgaggaat ctttcaaaac tcagtgaaag agaaaagaac      600
gagatgttcg aggaaatact gaaaaagag cgaatcgaca ggatctatct tgggaaaaaa       660
tacaccgtcc tcggtgaaag actggagttc gacgagaaaa atttgaggga tgctgctctg      720
gtgtactatg atgcgatcgc ccacgtggat atgatgtatc aaattttgaa agacgaaacc      780
```

```
ccggatatcg acttcgaagt gtcagttgac gaaacagaaa ctcccacgag tcctctcttc    840
cacattttcg ttgtggaaga actcagacga agaggtgtgg agttcaccaa tcttgccctg    900
agattcatcg gcgaatggga aagggaata ggttacaagg gggatcttgc acagttcgag    960
agagaaatca aaatgcacgc agaaatcgca aggatgttcg aaggatacaa aatatcactc   1020
cactctggaa gcgacaaatt ttccgtgtat cctgcttttg cttccgcgac aggaggcctt   1080
ttccacgtga agacagccgg aacgagttat cttgaggcgg tgaaggtcat atccatggtc   1140
aacccggagc tcttccggga gatctacagg tgtgctctcg atcactttga ggaagacaga   1200
aagtcctatc acatatctgc ggatctgtcg aaagttccgg aagtagagaa agtgaaagat   1260
gaagatcttc caggtctttt tgaagacatc aacgtgagac agttgatcca tgtcacctat   1320
ggctctgttc tgaaagatgc atctttgaaa gaacggctgt ttaagacgct tgaacaaaat   1380
gaggaactct tctacgagac cgtggcaaaa catataaaaa ggcacgtaga cctgttgaag   1440
gggtgactcg agcaccacca ccaccaccac tga                                1473
```

<210> SEQ ID NO 4
<211> LENGTH: 481
<212> TYPE: PRT
<213> ORGANISM: Artificial sequence
<220> FEATURE:
<223> OTHER INFORMATION: Hexuronate C4-epimeras

<400> SEQUENCE: 4

```
Met Val Leu Lys Val Phe Lys Asp His Phe Gly Arg Gly Tyr Glu Val
1               5                   10                  15

Tyr Glu Lys Ser Tyr Arg Glu Lys Asp Ser Leu Ser Phe Phe Leu Thr
            20                  25                  30

Lys Gly Glu Glu Gly Lys Ile Leu Val Val Ala Gly Lys Ala Pro
        35                  40                  45

Glu Gly Leu Ser Phe Phe Lys Lys Gln Arg Val Glu Gly Val Ser Phe
    50                  55                  60

Phe Phe Cys Glu Arg Asn His Glu Asn Leu Glu Val Leu Arg Lys Tyr
65                  70                  75                  80

Phe Pro Asp Leu Lys Pro Val Arg Ala Gly Leu Arg Ala Ser Phe Gly
                85                  90                  95

Thr Gly Asp Arg Leu Gly Ile Thr Thr Pro Ala His Val Arg Ala Leu
            100                 105                 110

Lys Asp Ser Gly Leu Phe Pro Ile Phe Ala Gln Gln Asp Val Arg Glu
        115                 120                 125

Asn Glu Arg Thr Gly Arg Thr Trp Arg Asp Val Leu Asp Ala Thr
    130                 135                 140

Trp Gly Val Phe Gln Glu Gly Tyr Ser Glu Gly Phe Gly Ala Asp Ala
145                 150                 155                 160

Asp His Ala Lys Arg Pro Glu Asp Leu Val Ser Ala Ala Arg Glu Gly
                165                 170                 175

Phe Thr Met Phe Thr Ile Asp Pro Ser Asn His Val Arg Asn Leu Ser
            180                 185                 190

Lys Leu Ser Glu Arg Glu Lys Asn Glu Met Phe Glu Glu Ile Leu Lys
        195                 200                 205

Lys Glu Arg Ile Asp Arg Ile Tyr Leu Gly Lys Lys Tyr Thr Val Leu
    210                 215                 220

Gly Glu Arg Leu Glu Phe Asp Glu Lys Asn Leu Arg Asp Ala Ala Leu
225                 230                 235                 240
```

```
Val Tyr Tyr Asp Ala Ile Ala His Val Asp Met Met Tyr Gln Ile Leu
                245                 250                 255

Lys Asp Glu Thr Pro Asp Ile Asp Phe Glu Val Ser Val Asp Glu Thr
            260                 265                 270

Glu Thr Pro Thr Ser Pro Leu Phe His Ile Phe Val Val Glu Glu Leu
        275                 280                 285

Arg Arg Arg Gly Val Glu Phe Thr Asn Leu Ala Leu Arg Phe Ile Gly
    290                 295                 300

Glu Trp Glu Lys Gly Ile Gly Tyr Lys Gly Asp Leu Ala Gln Phe Glu
305                 310                 315                 320

Arg Glu Ile Lys Met His Ala Glu Ile Ala Arg Met Phe Glu Gly Tyr
                325                 330                 335

Lys Ile Ser Leu His Ser Gly Ser Asp Lys Phe Ser Val Tyr Pro Ala
            340                 345                 350

Phe Ala Ser Ala Thr Gly Gly Leu Phe His Val Lys Thr Ala Gly Thr
        355                 360                 365

Ser Tyr Leu Glu Ala Val Lys Val Ile Ser Met Val Asn Pro Glu Leu
    370                 375                 380

Phe Arg Glu Ile Tyr Arg Cys Ala Leu Asp His Phe Glu Asp Arg
385                 390                 395                 400

Lys Ser Tyr His Ile Ser Ala Asp Leu Ser Lys Val Pro Glu Val Glu
                405                 410                 415

Lys Val Lys Asp Glu Asp Leu Pro Gly Leu Phe Glu Asp Ile Asn Val
            420                 425                 430

Arg Gln Leu Ile His Val Thr Tyr Gly Ser Val Leu Lys Asp Ala Ser
        435                 440                 445

Leu Lys Glu Arg Leu Phe Lys Thr Leu Glu Gln Asn Glu Glu Leu Phe
    450                 455                 460

Tyr Glu Thr Val Ala Lys His Ile Lys Arg His Val Asp Leu Leu Lys
465                 470                 475                 480

Gly

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
gggcatatga tggtcttgaa agtgttcaaa g                              31

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
aaactcgagc ccctccagca gatccacgtg                                30

<210> SEQ ID NO 7
<211> LENGTH: 33
<212> TYPE: DNA
<213> ORGANISM: Artificial Sequence
<220> FEATURE:
<223> OTHER INFORMATION: Primer
```

-continued

```
<400> SEQUENCE: 7
aaactcgagt cacccttca acaggtctac gtg                                              33
```